United States Patent [19]
Arimura et al.

[11] 4,313,938
[45] Feb. 2, 1982

[54] INTERFERON INDUCER AND METHOD OF PREPARING SAME

[75] Inventors: Hirofumi Arimura, Toyonaka; Masanori Nagai, Kyoto; Takeshi Yamauchi, Osaka; Tsutomu Kitagawa, Neyagawa; Tadakazu Suyama, Kyoto, all of Japan

[73] Assignee: The Green Cross Corporation, Osaka, Japan

[21] Appl. No.: 58,361

[22] Filed: Jul. 18, 1979

[30] Foreign Application Priority Data
Jul. 28, 1978 [JP] Japan .................... 53/92212

[51] Int. Cl.³ .................... A01N 9/00; C12P 19/34
[52] U.S. Cl. .................... 424/180; 424/85; 435/91; 435/194; 435/815; 435/816; 536/28; 435/948
[58] Field of Search .................... 435/91, 92; 536/27, 536/28; 424/85, 200, 180

[56] References Cited
U.S. PATENT DOCUMENTS
3,819,482  6/1974  Vidaver et al. .................... 435/91
4,082,613  4/1978  Thirumalachar et al. .......... 435/172

OTHER PUBLICATIONS
Microbiology, Davis et al., Harper & Rowe, Publishers, pp. 1398–1405 (1968).
Methods in Enzymology, vol. XXX, Part F, Moldave et al., pp. 654–661 (1974).

Primary Examiner—Alvin E. Tanenholtz
Attorney, Agent, or Firm—Cushman, Darby & Cushman

[57] ABSTRACT

Double-stranded RNA synthesized using native human DNA as template is found to be an excellent interferon inducer with low toxicity in spite of homologous native to host cell. It is produced by reacting ATP, GTP, CTP and UTP with one another in the presence of a native human DNA as template by the catalytic action of an active RNA polymerase to form RNA and subjecting the resulting RNA to annealing by heating it at a temperature of 70° to 100° C. and gradually cooling to room temperature or below to form double-stranded regions between their molecules.

4 Claims, 4 Drawing Figures

INTERFERON INDUCER AND METHOD OF PREPARING SAME

This invention relates to a kind of nucleic acid substances which induces interferon. More particularly it relates to an interferon inducer mainly composed of the same and the preparation of the interferon inducer.

Interferon (hereinafter referred to as IF) is a substance with an antiviral activity, and it is well known that animal cells produce it when they encountered various stimuli such as viruses and nucleic acids (Biology of Interferon: by Tsunataro Kishida, Published in 1971 by KINOKUNIYA SHOTEN).

Recently, IF is being proved to have an antitumor activity against osteogenic sarcoma which is a kind of malignant tumor (International Workshop on Interferon in the treatment of cancer, New York, 1975), and further it has been suggested that the chronic active hepatitis which is an intractable hepatitis B is also cured by high dose of IF (The New England Journal of Medicine, 295, (10), 517–522).

Because IF is a substance having a high biological activity as mentioned above, there have currently been made efforts of the improvement in mass production technology of IF by such a process as the induction and production from human leukocyte, human lymphoblastoid cells and the like.

On the other hand, since IF has species specificity against host cells, it is required to use the cells originated from human for the production of IF which is effective for human diseases. And the difficulties in industrial utilization of human cells have retarded the technical development thereof.

As a contrast of the above method which produces exogenous IF in vitro, attention has currently be given in another point of view to IF inducer which induces and increases endogenous IF in vivo. In order to obtain IF inducer which can be used as a medicine, the possibility to produce it has been pursued with making selection by various procedures. Examples of the IF inducers known so far include various kinds of viruses, nucleic acids, polysaccharides, extracts from microorganisms, and the like. Among them, nucleic acids are of the utmost interest due to their high activities. The IF inducibilities of nucleic acids previously confirmed are summarized in Table 1.

TABLE 1

| Kind of nucleic acids | IF inducibility* |
|---|---|
| homologous nucleic acids to host cell | − |
| heterologous nucleic acids to host cell | + |
| heterologous DNA to host cell | ± |
| heterologous RNA to host cell | + |
| heterologous single-stranded RNA to host cell | ± |
| heterologous double-stranded RNA to host cell | +++ |
| homologous DNA to host cell | − |
| homologous single-stranded RNA to host cell | |

*−none, ± ambiguous, + considerable, and +++ very strong.

Since Isaacs and his follower's hypothesis (Nature 197, 564 (1963), Lancet 11, 113 (1963)), it has been considered that the nucleic acid which induces IF is required to be heterologous to the host cell. Particular attentions against nucleic acids as an available IF inducer were not paid until it was found that heterologous double-stranded RNA to host cells had a strong potency to induce IF. Thus, attempts have currently been made on the production of double-stranded RNA from fungi, E. coli and other bacteria infected with phages, and the like. At about the same time, among synthetic double-stranded RNA's, Poly I:C is found to have a strong IF inducing activity, and today, especially heterologous double-stranded RNA to host cell, is well known to be effective as IF inducer among various nucleic acids. However, the heterologous RNA to host cell has side effects due to its heterologous characteristics, while it has a strong IF inducibility as mentioned above, and has intolerable toxicity in clinical application as a medicine, with the result that at present none is practically used in therapy of various diseases.

There was a general idea previously as mentioned above that it is essential for a nucleic acid-related IF inducer to be heterologous nucleic acid to host cells, and the persuit of a substance having a low toxicity was made among them with no results desirable. That is, the increase in IF inducing activity of nucleic acid-related IF inducer always accompanied by the increase in toxicity.

Therefore, the inventors changed the direction of studies to re-examination of homologous nucleic acid to host cell, which has been considered difficult to be developed due to the complete lacking of IF inducing activity. That is, the inventors studied on the pursuit and selection of those with high IF inducing activity from nucleic acids with low toxicity.

An attempt to select IF inducer from homologous nucleic acids to host cell as a prior art for the purpose mentioned above was made on providing a substance obtained by chemically modifying RNA extracted from human tissues (Japanese Patent Publication No. 2008/75). However, the substance thus obtained had very weak IF inducing activity under consideration and was insufficient as an IF inducer, though it had a considerable possibility as a medicine due to its low toxicity.

The inventors made further screening of homologous nucleic acid to host cell based on the teachings mentioned above, and applied an idea of heterologous double-stranded RNA to host cell having so far the most excellent IF inducibility as well as high toxicity correlated therewith to homologous double-stranded RNA as an candidate of the screening. That is, an attempt to synthesize double-stranded RNA was made using human DNA as template. As a result, unexpectedly, the inventors found that this substance mentioned above has such a low toxicity and excellent IF inducing activity as not to be found previously, and enabled this substance to be provided as a medicine and accomplished this invention.

An object of this invention is to provide a nucleic acid with low toxicity as well as excellent interferon inducing activity.

Another object of this invention is to provide an interferon inducer containing the said nucleic acid.

According to the present invention a double-stranded RNA was enzymatically synthesized using native human DNA as template and a process for the synthesis of the same.

The double-stranded RNA of this invention is enzymatically synthesized by a process which comprises reacting ATP, GTP, CTP and UTP with one another in the presence of a native human DNA as template by the catalytic action of an active RNA polymerase to form RNA and subjecting the resulting RNA to annealing by heating it at a temperature of 70° C. to 100° C. and gradually cooling to room temperature or below to form double-stranded regions between their molecules.

The native human DNA specified in this invention is prepared by extracting it from human tissues by an optional and known procedure, especially by extracting with a phenol, a phenol saturated with water, or a phenol saturated with a buffer solution.

For example, it is purified from human placenta according to a procedure by Parish et al. (J. H. Parish, and K. S. Kirby: Biochem. Biophys. Acta. 129, 554 (1966)), and Kirby et al. (K. S. Kirby, and E. A. Cook; Biochem. J., 104, 254 (1967)). It is summarized as that the frozen human placenta at −20° C. is homogenized in the presence of 6% sodium p-aminosalicylate and phenol-cresol mixture to effect extraction of nucleic acid and deproteinization. Deproteinization of the supernatant liquid obtained after centrifugation with phenol-cresol mixture is carried out once more. The nucleic acid is once precipitated from the supernatant obtained after centrifugation. The precipitated is dissolved in a low ionic strength solution and sodium chloride is added to high concentration to salting-out of RNA. After RNA is removed by centrifugation, residual RNA and highly aggregated DNA is removed. Then glycogen is removed by ultracentrifugation. From the supernatant, DNA is once precipitated and then dissolved in a low ionic strength solution. This solution is dialyzed against distilled water and the dialysate is subjected to lyophilization to obtain native DNA as lyophilized product.

Although a large variety of human tissues can be used and there is no limitation therefor, placenta and leukocyte generally available are usually used. Native DNA thus extracted is used as template in the polymerization of ribonucleoside triphosphates with the catalytic action of RNA polymerase to synthesize RNA. RNA polymerase usually means DNA-dependent RNA polymerase and is an enzyme which catalyzes the reaction for the synthesis of RNA by polymerization of ribonucleoside triphosphates through diester linkage using DNA as a template. This enzyme usually has a template specificity, that is, DNA extracted only from the same source with the enzyme is active as template. However, an active RNA polymerase used in this invention is required to be an enzyme having low template specificity, that is, can utilize human DNA as template for RNA synthesis. The words "active RNA polymerase" mentioned in the specification and claims means such enzyme as mentioned above. Enzymes obtained from *Micrococcus lysodeikticus* and *Escherichia coli* are generally available as those suitable for the above purpose, not being limited thereto.

For the isolation and purification of active RNA polymerase, for example, in the case where it is obtained from *Micrococcus lysodeikticus*, such a method that the original method of Nakamoto et al. (J. Biol. Chem., 239, 167 (1964)) is modified by introducing a part of the improved method of Weiss (Methods Enzymol., 12, 559 (1968)) can be applicable. In summarizing the steps, in general, the cells are harvested at the late logarithmic phase of its growth, stored under frozen state before use, washed and lysed with lysozyme at the time when used. To this crude extract streptomycin sulfate is added to concentrate nucleic acid-nucleoprotein complex, and after eluting RNA polymerase from the complex by adding phosphate buffer, streptomycin sulfate is again added to precipitate only nucleic acid selectively. This precipitate is removed by centrifugation, and membrane components and ribosome fraction are also removed by ultracentrifugation. Then protamine sulfate is added to form protamine-RNA polymerase complex, and RNA polymerase is eluted from the complex with phosphate buffer. RNA polymerase thus eluted is reacted with protamine sulfate to form the complex once more, subsequently eluted again from the complex with phosphate buffer, and the eluate is subjected to ammonium sulfate fractionation. The fraction precipitated with 30 to 50% saturation is collected and treated with cation exchanger to obtain purified RNA polymerase. The specific activity of RNA polymerase thus obtained is in the range of from 50 to 10,000 units/mg protein (Designation of unit: Methods Enzymol., 12, 559 (1968)).

Then the synthesis of RNA by RNA polymerase using native human DNA as template is carried out. Reactant mixture for the RNA synthesis contains 4 to 40 units/ml of RNA polymerase (units mentioned above), 100 to 1,000 μg/ml of DNA, 0.2 to 2 mM of ATP, GTP, CTP and UTP respectively as substrate, 1 to 4 mM of $MnCl_2$, 0 to 4 mM of spermidine hydrochloride, and 0.01 to 0.1 M of Tris-HCl (pH 7.0 to 8.0). The reaction temperature is in the range of from 20° to 40° C., and the reaction time is in the range of from 1 to 10 hours. Good yields are obtained in the range of from 2 to 4 hours of reaction time. The reaction is terminated by ice cooling, and additional treatments such as steps of the digestion of DNA by DNase (deoxyribonuclease) treatment, the removal of proteins by phenol treatment, the purification by dialysis, and the like, are carried out according to a method of Gumport et al (Biochemistry 8, 3168 (1969)). Then the dialysate is concentrated by ultrafiltration, and the concentrate is centrifuged on a CsCl cushion according to the method of Glisin et al. (Biochemistry 13, 2633 (1974)) to isolate RNA. RNA thus isolated is further purified by precipitation with ethanol, and the purified product is subjected to the following annealing reaction.

The annealing reaction for making RNA thus obtained double-stranded is carried out according to the method of Robinson et al (J. Biol. Chem., 239, 2944 (1964)). The reaction is effected in such a way that RNA is dissolved in two fold the concentration of SSC (standard saline citrate, 0.15 M NaCl, 0.015 M sodium citrate) and a pH value of from 6.5 to 7.5, and the resulting solution is heated at a high temperature of from 70° to 100° C., and then the temperature is gradually cooled to room temperature to terminate the reaction. In this case it is preferable that the resulting solution is once heated at the temperature of 70° to 100° C. for 3 to 10 minutes and is quickly cooled to room temperature, and then heated again to the same temperature as above followed by being cooled gradually to room temperature. In the annealing step it is also preferable to maintain at a temperature between the high temperature and room temperature for a considerable time. Thus, after the reaction is completed, RNA is recovered as precipitate by ethanol precipitation and the like, the resultant precipitate is centrifuged and washed, and then redissolved in an aqueous sodium chloride solution of low concentration, subjected to dialysis against water at a low temperature for 10 to 30 hours, and if required, sterilized by filtration, and then subjected to lyophilization to obtain a preparation.

The thus obtained interferon inducer of a double-stranded RNA synthesized with native human DNA as template exhibits white color, is tasteless, odorless, possesses at least about 4%, normally 10-15% of double-stranded moiety in its molecule, and has the following physical and chemical properties. The samples used were those obtained by repeating the process of Example 1.

The physical and chemical properties of the interferon inducer containing double-stranded RNA are shown in attached drawings.

FIG. 1 of the drawings shows the sedimentation pattern of a sample in a sucrose density gradient centrifugation. Radioactivity (dpm) was mesured with respect to a sample obtained in (3) of the Example 1, provided that (8-14$_C$) ATP (5 $\mu$Ci/ml) was used in place of the normal ATP used therein.

(1) Molecular weight

Figure 1:
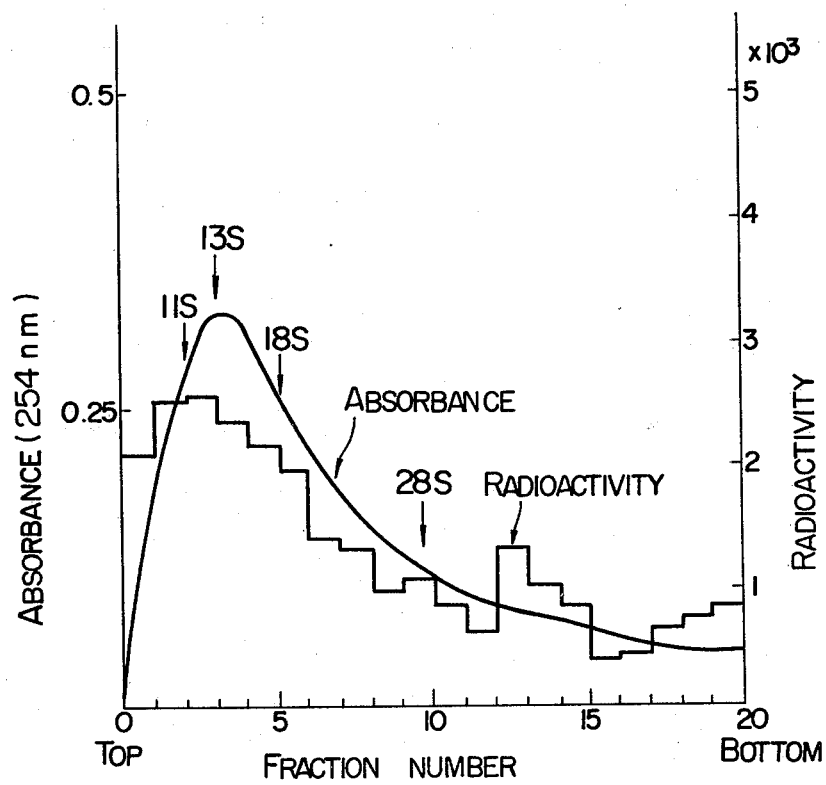

Sedimentation coefficient was determined by sucrose density gradient centrifugation (5-20% in Spinco SW 50.1 rotor, 38,000 r.p.m., 3.5 hrs), using mouse L cell ribosomal RNA as a standard. The sample was mainly composed of 11 to 13s components (FIG. 1).

(2) Solubility

Soluble in distilled water, 0.01 M Tris-HCl buffer (pH 7.5), two-fold the concentration of SSC (loc. cit.), 0.1 fold the concentration of SSC (pH 7.0), and the like. Insoluble in ethanol and acetone.

Figure 2:
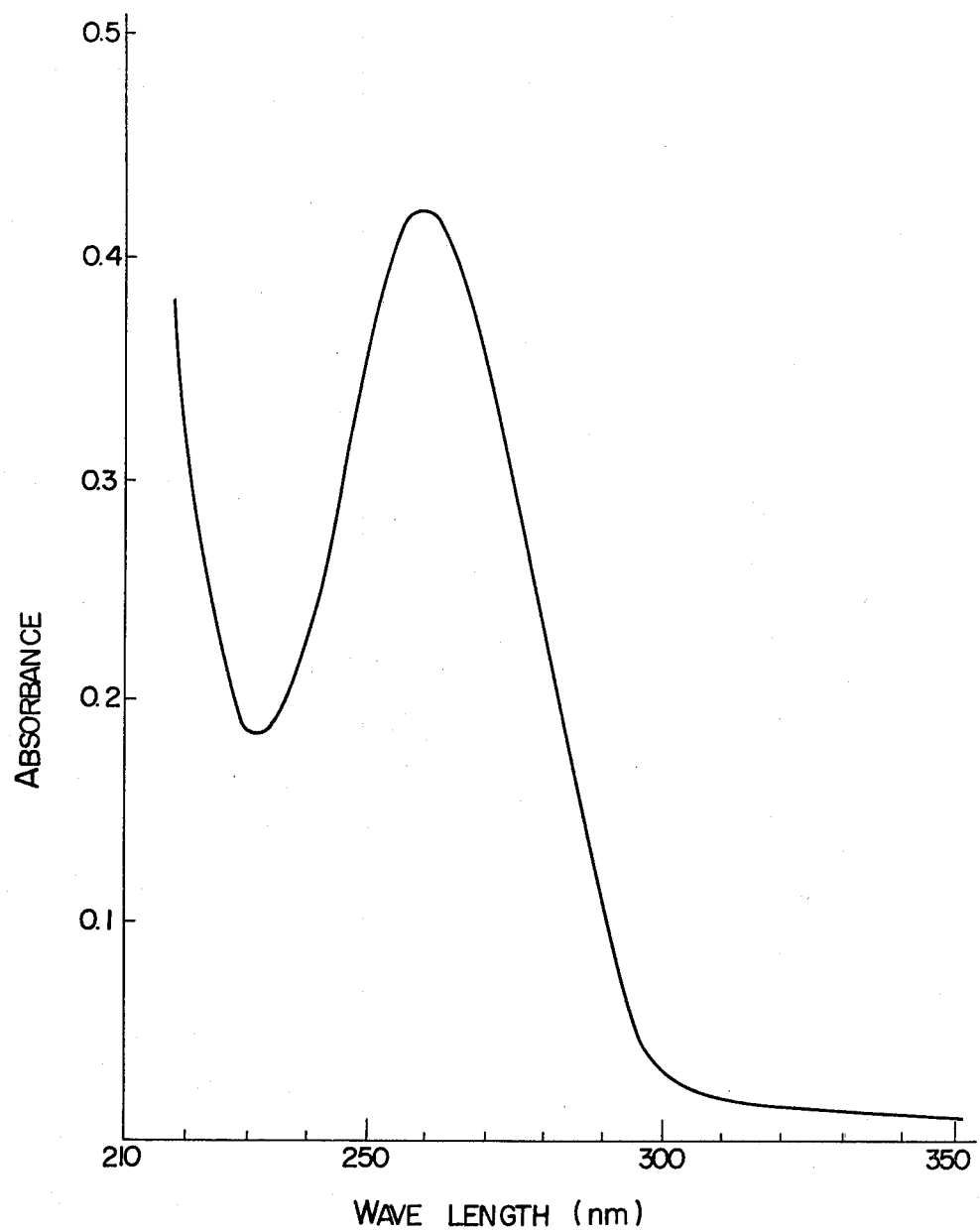
FIG. 2 shows the ultraviolet absorption spectrum.

(3) Ultraviolet Absorption Spectrum 0.02 mg/ml aqueous solution of the sample gave a typical ultraviolet absorption spectrum for nucleic acid (FIG. 2). The maximum absorbance was at 260 nm and the minimum one at 230 nm.

(4) Colour Reaction

It was positive to orcinol test, negative to diphenylamine test and indole test, and showed a colour reaction characteristic of RNA.

(5) Precipitation Reaction

To 0.5 mg/ml aqueous solution of the sample two-fold volume of ethanol was added and allowed to stand more than one hour at −20° C. Almost 100% of the material was precipitated. Addition of half the volume of cold 50% TCA (trichloroacetic acid) to 0.1 mg/ml aqueous solution of the sample made 80 to 90% of the RNA TCA-insoluble which could be collected by Millipore filter (0.45 $\mu$m).

(6) Digestion by ribonuclease

The sample was dissolved in two fold the concentration of SSC (pH 7.0) and treated with bovine pancreatic ribonuclease (10 $\mu$g/ml) and ribonuclease-T$_1$ (1 $\mu$g/ml) at 37° C. for 30 minutes. As the result about 11 to 13% of the sample was remained undigested. On the other hand, the sample was dissolved in 0.3 fold the concentration of SSC (pH 7.0), heated and quickly cooled, and thereafter treated with ribonuclease as mentioned above after bringing the solution to two fold the concentration of SSC. As a result 2 to 3% was not digested.

(7) Digestion by Deoxyribonuclease

The sample was dissolved in 0.01 M Tris-HCl buffer (pH 7.4) and treated with deoxyribonuclease (50 $\mu$g/ml) at 37° C. for 30 minutes with the result that the proportion of TCA-insoluble fraction was the same as that before the treatment, and that no increase in absorbance at 260 nm between before and after the treatment.

(8) Sensitivity to Alkaline Hydrolysis

The sample was dissolved in 0.3 N potassium hydroxide and incubated at 37° C. for 18 hours. The sample was completely hydrolyzed. Analysis of the hydrolyzate by thin-layer chromatography revealed only the spots of adenylic acid, guanylic acid, cytidylic acid and uridylic acid.

(9) Base Composition

Analysis of base composition was carried out by thin-layer chromatography technique with respect to the alkali hydrolyzate obtained according to (8). As the result of analysis of molar ratio of each nucleotide, it was in the range of from 27.0 to 30.5% of adenylic acid, 20.6 to 24.7% of guanylic acid, 16.8 to 24.3% cytidylic acid, and 27.8 to 32.7% of uridylic acid.

(10) Buoyant Density in Cs$_2$SO$_4$

Buoyant density in Cs$_2$SO$_4$ of the sample measured by ultracentrifugation (Spico SW 50.1 rotor, 31,500 rpm, 72 hr) was in the range of from 1,635 to 1,640.

(11) Tm (thermal Denaturation of RNase-resistant RNA)

Figure 3:
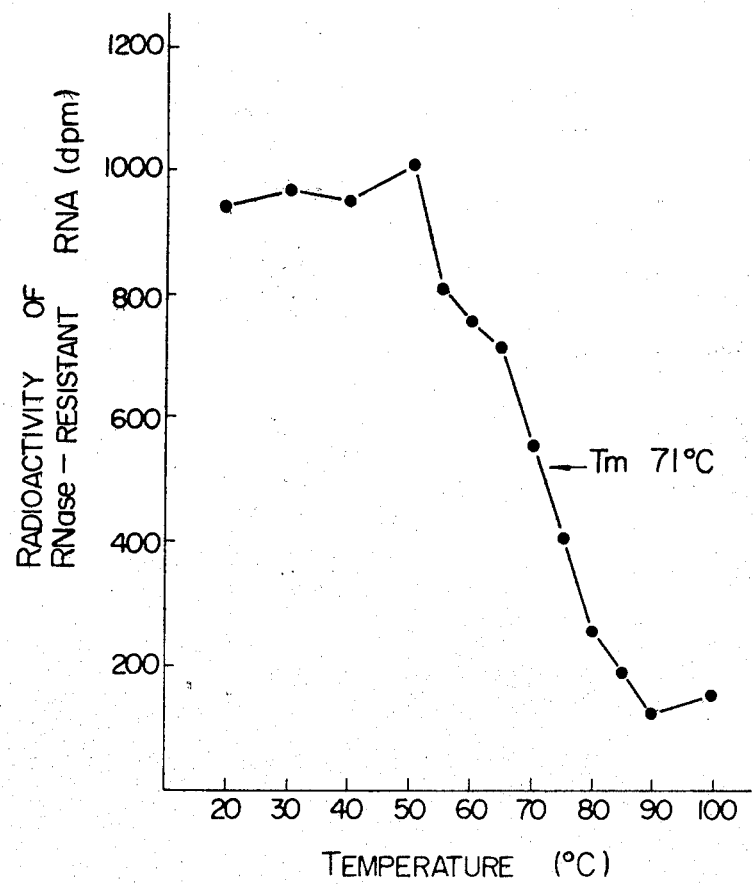
FIG. 3 shows the thermal denaturation curve of RNase-resistant RNA. The thermal denaturation was measured with respect to the radioactive sample as above which was heated at various temperatures and then subjected to RNase treatment.

The sample was dissolved in 0.1 fold the concentration of SSC (pH 7.0) and Tm (melting temperature) was determined according to the method of C. Colby and D. H. Duesberg (Nature, 222, 940 (1969)). Tm was 71° C. (FIG. 3).

(12) Increase in Absorbance with increasing Temperature

Figure 4:
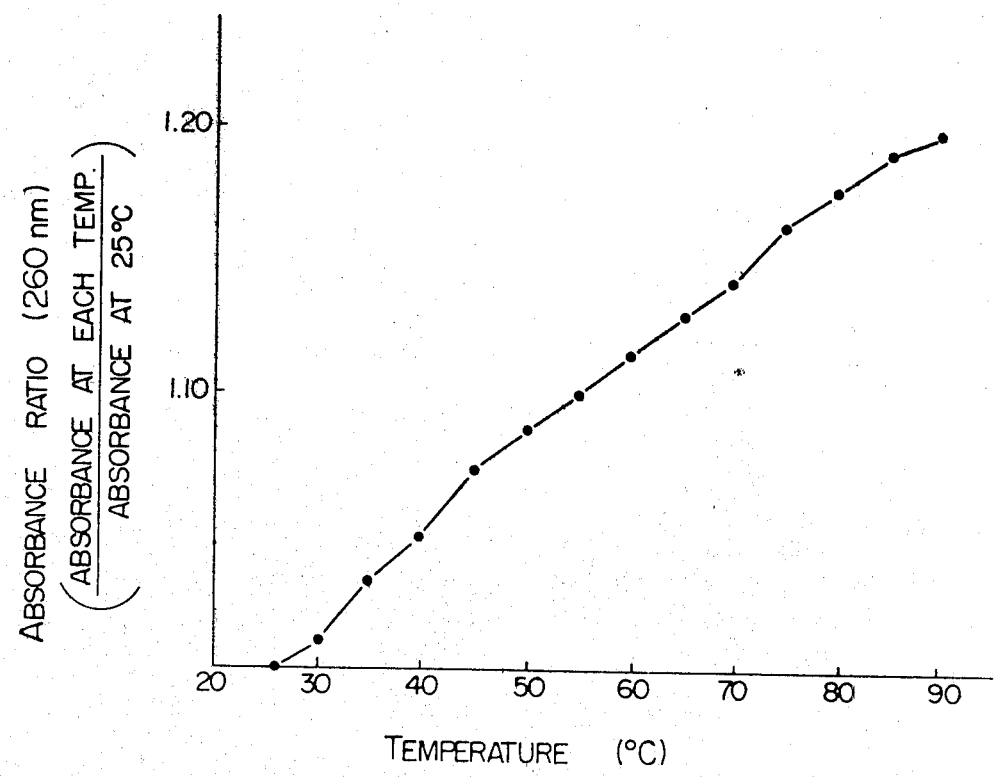
FIG. 4 shows absorbance ratios at 260 nm, that is, the ratio of absorbances at various temperatures to that at 25° C.

The sample was dissolved in 0.1 fold the concentration of SSC (pH 7.0) and the increase in absorbances at 260 nm as temperature increases was determined. An increase by about 20% was observed in the range of from 25° C. to 90° C. (FIG. 4).

(13) Purity

Assessment of the purity of the sample was carried out as below:

The amount of protein was determined by Folin-Lowry method, and the amount of DNA was determined by the SST method modified by Mizuno et al. ("General Method of Separation and Quantitative Analysis of Nucleic Acid", pp 23, edited by Uzitani et al., Published by Tokyo University Publication (1969)). As the result no contamination of protein and DNA was observed.

(14) Electron Microscopic Observation

The electron microscopic observation carried out according to the method of Kleinschmidt et al. [J. Molec. Biol. 10, 282 (1964)] showed that most RNA molecules were linear and in the range of from about 0.1 to 3$\mu$ in length.

The double-stranded RNA of the invention, which has the physical and chemical properties as described above can be used as IF inducer because it induces IF and, moreover, has extremely low toxicity as apparent from the results of Experimental Examples hereinafter described.

In making medical preparation various kinds of stabilizers such as human albumin, mannitol etc., solubilizing agents such as glycine and excipients such as sorbitol and others may be added to the solution containing the active material prior to lyophilization as mentioned above. When used, the medical preparation thus prepared is dissolved in saline, sterilized water, sterilized isotonic solution for injection, and the like, and is administered to patients as IF inducer by intravenous injection, muscular injection and subcutaneous injection.

An effective dose is considered to be in the range of from 1 μg to 2 mg per kg body weight per day, but the amount of dose can be increased, if necessary.

The preparation of this invention is effective as medicine even in a crude state, that is, in a mixed state with single-strained RNA, and 4% or more as the amount of double-stranded RNA is sufficiently effective.

Biological properties of the preparation of this invention are described in detail by way of Experiments.

EXPERIMENTAL EXAMPLE 1

Antiviral Activity In Vitro

Antiviral activity was determined by measuring virus yield according to the partially modified method of the method of Billiau et al. (Proc. Soc. Exp. Biol. Med. 132, 790, (1969)). That is, 0, 0.1, 1, 10 and 50 μg/ml of inducer samples (preparation of this invention and Poly I:C as a control), 50 μg/ml of DEAE-dextran (M.W. $50 \times 10^4$: produced by Pharmacia, Sweden) and 3 ml of Eagle's minimal essential medium (referred to as Eagle MEM hereinafter) supplemented with 0.5% foetal calf serum were added onto monolayer cells (2.5 to $3.0 \times 10^6$ cells/bottle) in 50 ml-culture bottle, and incubated at 37° C. for 20 hours. After incubation, Eagle MEM containing the inducer was removed, and the cells were washed with Hanks salt solution three times, then Vesicular stomatitis virus (V.S.V.) was added thereon at a multiplicity of infection 2 to 3 plaque forming unit (p.f.u.)/cell. Viruses were adsorbed at 37° C. for one hour. After adsorption, the cells were washed five times to remove free V.S.V., 5 ml of a new maintenance medium (Eagle MEM containing 1% foetal calf serum) were added. After the incubation at 37° C. for 20 hours, the cells were harvested in a freezer at −30° C., freezing-thawing were repeated twice, then they were centrifuged (2,000 r.p.m. 10 minutes). The titer of V.S.V. in the supernatant was determined by plaque assay on FL cell cultures. Virus yield from the cells treated in Eagle MEM free of inducers (containing DEAE-dextran and serum) was taken as a control.

The cells used herein were two kinds of established cell lines of human amniotic FL cells and rabbit kidney RK-13 cells, as well as human embryonic foreskin diploid cell (HFS cells), and human embryonic kidney HK cells. HFS cells were purchased from Flow Laboratories Inc. (Flow-7000 cell) and passaged 25 to 27 times. Heteroploid cells of HK cells were originally cultured by the inventors and passaged about 130 times thereafter.

These cells were grown in Eagle MEM supplemented with 10% foetal calf serum, 100 ut/ml penicillin G, 100 μg/ml streptomycin sulfate, and 60 μg/ml kanamycin. When viruses were inoculated, cells were cultured in maintenance medium in which the amount of serum was reduced to 1%. Cells were cultivated in $CO_2$ incubator (5% $CO_2$).

Poly I:C used as control was purchased from Miles Laboratories, Inc. (U.S.A.). This was dissolved in phosphate buffer (pH 7.0) at 2.5 mg/ml, stored at −30° C. and diluted when used.

The results are shown in Table 2, that is, although there is a little difference between cells, the preparation of this invention has almost the same antiviral activity as poly I:C.

TABLE 2

| Host cells | Concentration of inducer (μg/ml) | Virus yield (p.f.u./ml)* | |
|---|---|---|---|
| | | Preparation of the invention | Poly I:C |
| FL (human) | 0 | $6 \times 10^7$ | $6 \times 10^7$ |
| | 0.1 | $1 \times 10^7$ | $8 \times 10^6$ |
| | 1 | $2.4 \times 10^4$ | $7.5 \times 10^3$ |
| | 10 | $3.3 \times 10^3$ | $4 \times 10^2$ |
| | 50 | $2 \times 10^2$ | $1.5 \times 10^2$ |
| HK (human) | 0 | $7.5 \times 10^7$ | $7.5 \times 10^7$ |
| | 0.1 | $4.5 \times 10^7$ | $5 \times 10^7$ |
| | 1 | $1 \times 10^6$ | $1.6 \times 10^6$ |
| | 10 | $4 \times 10^4$ | $3.3 \times 10^4$ |
| | 50 | $1.5 \times 10^3$ | $2\ 33\ 10^3$ |
| RK-13 (rabbit) | 0 | $1 \times 10^7$ | $1 \times 10^7$ |
| | 0.1 | $1.5 \times 10^4$ | $9 \times 10^3$ |
| | 1 | $5 \times 10^3$ | $1 \times 10^3$ |
| | 10 | $3.3 \times 10^2$ | $2.3 \times 10^2$ |
| | 50 | $2 \times 10^2$ | $2 \times 10^2$ |

*p.f.u.: plaque forming unit

EXPERIMENTAL EXAMPLE 2

Induction of IF In Vitro

IF inducing activity was tested on addition of the preparation of this invention to cultured cells. The test was carried out by the application of superinduction technique according to the method of Vilcek et al. [PB-266, 670 (1967)]. That was, 2 ml of Eagle MEM (free of serum) containing 5 to 50 μg/ml of inducer and 100 μg/ml of cycloheximide (produced by Nakarai Chemicals Co.) was added on HFS cells which had formed monolayer in a plastic petri dish of 6 cm in diameter, and the cells were incubated at 37° C. for 5 hours.

Then, 0.5 ml of Actinomycin-D (Produced by Becton Dickinson Co.) was added to the medium, so that the final concentration became 1 μg/ml. The incubation was further effected at 37° C. for one hour. After the completion of 6 hours' incubation in total, the cells were washed 5 times with Hanks salt solution, 5 ml of Eagle MEM supplemented with 0.5% of serum was added. After 20 hours incubation at 37° C., the medium was collected and centrifuged (1,000 r.p.m., for 5 minutes) to obtain the supernatant including IF, and the IF titer was determined using FL cells.

IF titer was assayed by the modified method of Vilcek et al. [J. gen. Virol. 2, 648 (1968)]. Monolayer cell cultures in a plastic petri dish of 6 cm in diameter were washed and inoculated with serial two fold dilutions of IF sample in Eagle MEM containing 0.5% foetal calf serum, and incubated at 37° C. for 20 hours. After the cell sheets were washed, they were challenged with about 100 p.f.u./plate of V.S.V. and plaques produced were counted after further 2 or 3-days incubation. IF titer was expressed as the reciprocal of the number of dilution of the sample which reduced the plaque number to 50% of control receiving Eagle MEM in place of the sample. The titer of IF sample of human cells was determined by simultaneously determining the human leukocyte standard IF to convert it to international unit (IU). Poly I:C was used as a control.

The results are shown in Table 3. Thus, the preparation of this invention shows more excellent IF inducing activity than poly I:C.

TABLE 3

| Concentration (μg/ml) | Preparation of this invention | Poly I:C |
|---|---|---|
| 0 | <10 | <10 |
| 5 | 200 | 50 |

TABLE 3 -continued

| Concentration (μg/ml) | Preparation of this invention | Poly I:C |
|---|---|---|
| 50 | 350 | 80 |

EXPERIMENTAL EXAMPLE 3

Induction of IF In Vivo

Male rabbits, weighing 2.0 to 2.5 Kg received an intravenous injection of 10 or 100 μg/Kg of the preparation of this invention or poly I:C as a control and were bled just before administration and 1, 2, 4, 8, 11 and 24 hours after administration.

IF inducing activities of inducers administered were determined by assaying IF contents in collected sera. The method of IF titration was similar to that of Vilcek et al. mentioned above except that RK-13 cells were used instead of FL cells.

The results are shown in Table 4, that is, the preparation of this invention shows an inducing activity for IF production in vivo equal to or higher than that of Poly I:C.

TABLE 4

| Hour after administra- tion | IF titer* (unit/ml serum) | | | |
|---|---|---|---|---|
| | Preparation of this invention | | Poly I:C | |
| | 10 μg/kg | 100 μg/kg | 10 μg/kg | 100 μg/kg |
| 0 | 25 | 35 | 20 | 20 |
| 1 | 180 | 300 | 180 | 250 |
| 2 | 2200 | 9500 | 1600 | 8000 |
| 4 | 800 | 5000 | 600 | 2000 |
| 8 | 280 | 350 | 200 | 300 |
| 11 | 160 | 240 | 100 | 150 |
| 24 | 40 | 90 | 60 | 80 |

*IF titer represents an average value of a group of two rabbits.

The characteristics of IF produced by the inducer of this invention were tested with respect to host cells species specificity, non-specificity against challenge viruses, sensitivity to trypsin-treatment, insensitivity to RNase treatment and pH 2-treatment, and ultracentrifugation treatment (100,000×g, 3 hours). Thus it was confirmed that the material was nothing but IF.

EXPERIMENTAL EXAMPLE 4

Toxicity Test

The effects of the present preparation of this invention and Poly I:C as a control on multiplication of cultured cells was examined. Four ml of the human amniotic FL cell suspension (60×10$^4$ cells/4 ml) in growth medium was placed in 5 ml-culture bottle, and 1 ml of Eagle MEM containing 5, 50 and 250 μg/ml (These were diluted to 5 fold finally) of the preparation respectively was simultaneously added thereto. The cells were cultured stationarily at 37° C. for 6 days.

After 2, 4, and 6 days cultivation, two bottles in each group were taken out, and cells were washed with phosphate buffer to remove floating cells. And the cells remained were detouched from the glass surface with the aid of ethylenediaminetetraacetate (EDTA) (0.02%) and trypsin (0.25%) for counting of the cell number. Then visible cells number was counted by means of erythrocine B staining and hemocyto meter.

The result shown in Table 5 indicates that poly I:C is somewhat toxic even at a concentration of 1 μg/ml, a remarkably toxic at 10 μg/ml, and at the level of 50 μg/ml almost no cell multiplication is observed. On the contrary, the preparation of this invention has no toxicity at a concentration of 10 μg/ml or less, and the cell multiplication is only slightly suppressed as compared with control even at a concentration of 50 μg/ml.

From the above experiments, the preparation of this invention is found to be IF inducer which has an antiviral activity approximately equal to, or higher than, Poly I:C, and has less toxicity as compared therewith.

TABLE 5

| Concentration of inducer added | Days culti- vated | Viable cell number* (× 10$^4$ cells/bottle) | |
|---|---|---|---|
| | | Preparation of this invention | Poly I:C |
| 0 | 0 | 62 | 62 |
| μg/ml | 2 | 112 | 112 |
| | 4 | 168 | 168 |
| | 6 | 273 | 273 |
| 1 | 0 | 62 | 62 |
| μg/ml | 2 | 126 | 88 |
| | 4 | 183 | 133 |
| | 6 | 286 | 219 |
| 10 | 0 | 62 | 62 |
| μg/ml | 2 | 109 | 54 |
| | 4 | 174 | 71 |
| | 6 | 279 | 114 |
| 50 | 0 | 62 | 62 |
| μg/ml | 2 | 99 | 37 |
| | 4 | 154 | 45 |
| | 6 | 247 | 83 |

*Viable cell number represents an average value of two bottles

EXPERIMENTAL EXAMPLE 5

Acute Toxicity

Acute toxicity was tested for the preparation of the invention by use of C$_{57}$BL male mice according to the method of Lichied and Wilcoxon (Journal of Pharmacology and Experimental Therapeutics, 90, 99, (1949)).

The result showed that no mice died on intraperitoneal administration of the preparation at a level of 50 mg/Kg of body weight, or on intravenous administration at a level of 25 mg/Kg.

LD$_{50}$ in mice was not less than 50 mg/Kg for the preparation given subcutaneously, or not less than 25 mg/Kg for the preparation given intravenously.

The process for the preparation of this interferon inducer will be illustrated in the following Examples. The gist of this invention comprises that double-stranded RNA is produced by annealing of the RNA synthesized by the action of RNA polymerase of low template specificity and native human DNA as template. The invention is not to be limited to the disclosure in the following Examples. The symbols, % (W/V) and (V/V) therein mean percentage showing solutes in unit weight and unit volume, respectively, in unit volume of a solution.

EXAMPLE 1

(1) Isolation and purification of human placenta DNA

The placenta frozen immediately after parturition and stored at −20° C. was broken into pieces to 60 g of which 15 volumes of 6% sodium p-aminosalicylate and 15 volumes of phenol-cresol mixture (composition: phenol 500 g, m-cresol 70 ml, water 55 ml and 8-hydroxylquinoline 0.5 g) were added, and the resulting mixture was homogenized at room temperature for one minute with a mixer at the maximum rotation. The suspension thus obtained was stirred at room temperature for 20 minutes, and then centrifuged at 6,000×g at 5° C. for 30 minutes to remove denatured protein and phenol. To the supernatant was added sodium chloride so that its final concentration became 3% (W/V), and again half the volume of the supernatant of the phenol-cresol mixture. The mixture was stirred at room temperature for 20 minutes, and then centrifuged at 8,000×g at 5° C. for 10 minutes.

To the supernatant two volumes of cooled ethyl alcohol-cresol mixture (volume ratio, 9:1) was added and mixed gently to form a precipitate. After the fibrous precipitate was spooled with a glass rod, the remaining liquid was allowed to stand at 2° C. for one hour, and then remaining precipitate was recovered by centrifugation. The combined precipitate was well washed with a sufficient volume of 75% ethyl alcohol containing 2% sodium acetate, and was dissolved completely in 200 ml of 0.1 M sodium acetate containing 5 mM sodium fluoride. Subsequently sodium chloride was added to this solution to a final concentration of 3 M. This solution was allowed to stand at a temperature of from −2° to −5° C. for 15 hours, and centrifuged at 12,000×g at 5° C. for 10 minutes. The supernatant was added with an equal volume of cold ethyl cellosolve and mixed gently to form a white fibrous precipitate. After allowing to stand for 20 minutes in an ice-bath, the fibrous precipitate was taken out with a glass rod, dispersed and dissolved at room temperature in 300 ml of 3 M sodium acetate buffer solution (pH 6.0) containing 5 mM sodium fluoride. After dissolution was almost completed, the solution was centrifuged at 2,000×g at 5° C. for 10 minutes to remove the residual RNA and highly aggregated DNA as precipitate.

To the supernatant an equal volume of cold ethyl cellosolve was added, and the mixture was allowed to stand for 20 minutes in an ice-bath. The fibrous precipitate formed was spooled with a glass rod, and dispersed and dissolved at room temperature in 200 ml of 0.1 M sodium acetate buffer solution (pH 6.0) containing 5 mM of sodium fluoride. After the dissolution was almost completed, the solution was centrifuged at 60,000×g at 5° C. for 90 minutes to remove glycogen as precipitate.

To the supernatant sodium acetate was added to a final concentration of 0.3 M, and mixed with an equal volume of cooled ethyl cellosolve. After allowing to stand 20 minutes in an ice-bath, the fibrous precipitate was spooled with a glass rod, and dissolved in 16 ml of 0.1 M sodium acetate buffer (pH 6.0) containing 5 mM of sodium fluoride.

After dissolution was completed, the solution was transferred to dialysis tubing and dialyzed for 48 hours at 2° to 5° C. against 200 ml of distilled water with five changes of the outside solution. The dialysate was centrifuged to remove insoluble materials, and the concentration of DNA was determined by measuring an absorbance at 260 nm of the diluted supernatant.

The calculatoin of concentration was carried out by taking absorbance at 260 nm of DNA 1 mg/ml solution is 20. Solutions containing 6.5 mg of DNA were placed in 10 ml-vials respectively, and subjected to lyophilization. Fourty mg of human DNA in total were obtained by the above procedures. For the assessment of the purity of the DNA preparation obtained, the amount of protein was determined according to the improved method of Lowry et al. (J. Biol. Chem., 193, 265 (1951)), and the amount of RNA was determined by the method of Mizuno (Shigeki Mizuno: "General Method of Isolation Quantitative Analysis of Nucleic Acid", pp. 23; edited by Ujitani et al., published by Tokyo University Publication (1969)), which improved the method of "DNA.RNA Fractional Quantitative Analysis" of Schmidt-Thannhauser-Schneider. The amount of protein was 0.4% in terms of human placenta albumin, and the amount of RNA was 4.8% in the total nucleotide.

(2) Purification of RNA polymerase

*Micrococcus lysodeikticus* was grown in Nutrient Broth using a Jar Fermenter, harvested when reached a late logarithmic phase of growth, and stored frozen at −20° C. Four hundred grams of the frozen cells was dispersed in 2 l of 0.01 M Tris-HCl buffer (pH 8.0), and centrifuged to collect the washed cells. Washed cells were dispersed in 0.01 M Tris-HCl buffer (pH 8.0) containing 0.2 M surcose to make the final volume of 2l. To this suspension 600 mg of hen egg white lysozyme was added, and the suspension was incubated at 30° C. After 15 minutes incubation, 6 ml of 0.1 M $MgCl_2$ was added and further incubated for 45 minutes to destroy cell wall. Thereafter, 18 ml of 0.1 M $MgCl_2$ and 2,400 ml of ice-cooled water were added. The mixture was stirred vigorously in an ice-bath. The following procedures hereinafter were all conducted in an ice-bath. Ten minutes later, 600 ml of 10% (W/V) streptomycin sulfate were added, and further 10 minutes later the precipitate produced was centrifuged at 20,000×g at 5° C. for 10 minutes. The precipitate obtained was suspended in 800 ml of 0.01 M Tris-HCl buffer (pH 8.0) containing 0.2 M sucrose, 0.1% streptomycin sulfate was 0.00025 M $MgCl_2$. Ten minutes later, the suspension was centrifuged at 20,000×g at 5° C. for 10 minutes. The precipitate was homogenized in 720 ml of a solution, which was prepared by mixing 8 ml of 1 M potassium phosphate buffer (pH 7.5), 8 ml of 0.1 M $MgCl_2$ and 80 ml of 2 M sucrose, and diluting the mixture with distilled water up to 720 ml, by use of Potter-Elvejhem's Teflon homogenizer. To this homogenate were added 32 ml of 1 M potassium phosphate buffer (pH 7.5) and 10 minutes later 70 ml of 10% streptomycin sulfate additionally. After 10 minutes' stirring the precipitate formed was separated by centrifugation at 30,000×g at 5° C. for 30 minutes, and the supernatant obtained was further centrifuged at 105,000×g at 5° C. for 2 hours to remove membrane components and ribosomal fraction.

To 800 ml of the supernatant obtained by the ultracentrifugation were added 110 ml of 1 M potassium phosphate buffer (pH 7.5), and further 160 ml of 2.5% unneutralized protamine sulfate to precipitate RNA polymerase as a complex with protamine sulfate. After 10 minutes' stirring the precipitate was collected at 20,000×g by centrifugation at 5° C. for 10 minutes. The precipitate was homogenized in 180 ml of 0.2 M potassium phosphate buffer (pH 7.5) containing 0.2 M sucrose to elute RNA polymerase. After 10 minutes' stirring, the suspension was centrifuged at 30,000×g at 5° C. for 10 minutes. To the supernatant 360 ml of 0.1% unneutralized protamine sulfate solution was added, and again RNA polymerase was precipitated as a complex with protamine sulfate. After 10 minutes' stirring the suspension was centrifuged at 20,000×g at 5° C. for 15 minutes. The precipitate was homogenized in 50 ml of 0.14 M potassium phosphate buffer (pH 7.5) containing 0.2 M sucrose and the homogenate was centrifuged at 30,000×g at 5° C. for 10 minutes. The collected precipitate was homogenized in 30 ml of 0.2 M potassium phosphate buffer (pH 7.5) containing 0.2 M sucrose to elute RNA polymerase. After 10 minutes' stirring, the suspension was centrifuged at 30,000×g at 5° C. for 15 minutes. To the supernatant (30 ml) 7.27 g of ammonium sulfate was added so as to be 40% saturation to effect ammonium sulfate fractionation. Fifteen minutes after the addition of ammonium sulfate, the suspension was centrifuged at 30,000×g at 5° C. for 10 minutes. The precipitate was dissolved in 5 ml of 0.02 M Tris-HCl buffer (pH 7.5) containing 0.3 M ammonium sulfate, and an equal volume of glycerol was added. The solution was 2.5 fold diluted with 0.01 M Tris-HCl buffer (pH 7.5), and passed through CM-cellulose column in a glass filter, which had been prepared by using 2.4 g of CM-cellulose, to remove ribonucleases. The column was washed with 0.01 M Tris-HCl buffer (pH 7.5) containing 20% glycerol and 0.06 M ammonium sulfate, and the eluate was passed through CM-cellulose column which had been prepared by use of 0.8 g CM-cellulose.

After the column was washed, 22.2 g of ammonium sulfate was added to 80 ml of the total eluate to effect ammonium sulfate precipitation. Fifteen minutes later, the precipitate formed was collected by centrifugation at 30,000×g at 5° C. for 15 minutes, and the precipitate thus collected was dissolved in 4 ml of 0.02 M Tris-HCl buffer (pH 7.5) containing 0.3 M ammonium sulfate, and further an equal volume of glycerol was added, and stored at −70° C. before use.

From 400 g frozen cells, 43 mg of RNA polymerase preparation with a specific activity of 190 units per mg of protein (total activity is 8,200 units) and a 280:260 nm absorbance ratio of 1.55 was obtained.

One unit of enzyme activity was defined as the amount catalyzing the incorporation of 1 n mole of $^{14}C$-ATP into TCA-insoluble material during 10 minutes of incubation.

(3) Synthesis, Isolation and Purification of RNA

The reagents used in RNA synthesis were similar to those used in RNA polymerase assay system by Weiss (Methods. Enzymol., 12, 559 (1968)). Each reagent was dissolved in 0.1 M Tris-HCl buffer (pH 7.5), and shown in the following Table 6.

TABLE 6

| Reagents in RNA synthesis system, Total 500 ml. | | |
|---|---|---|
| Reagents | Concentration | Total amounts |
| Purified RNA polymerase | 20 units/ml | 10,000 units |
| Human placenta DNA | 200 μg/ml | 100 mg |
| ATP | 0.4 mM | 200 μmoles |
| CTP | 0.4 mM | 200 μmoles |
| UTP | 0.4 mM | 200 μmoles |
| GTP | 0.4 mM | 200 μmoles |
| $MnCl_2$ | 2.5 mM | 1,250 μmoles |
| Unneutralized spermidine trihydrochloride | 2 mM | 1,000 μmoles |
| Tris-HCl, pH 7.5 | 0.1 M | 50 m moles |

The above reagents were mixed well and incubated for 3 hours at 30° C. in a water bath. Thereafter, the reaction mixture was cooled in an ice-bath to terminate the reaction, and heated for 5 minutes at 65° C. to inactivate RNA polymerase. The reaction mixture was cooled to about 37° C. with tapped water, and then 56 ml of 0.1 M $MgCl_2$ was added to bring the solution to 10 mM. Further 5.6 mg of DNase (free of ribonuclease) was added and incubated at 37° C. for 30 minutes to digest DNA.

The reaction mixture was heated at 100° C. for 3 minutes to inactivate DNase, and then cooled to room temperature with tapped water. Thereafter 560 ml of two-fold the concentration of SSC (pH 7.0) and 1120 ml of phenol-cresol mixture (composition: phenol 500 g, m-cresol 70 ml, water 55 ml, 8-hydroxyquinoline 0.5 g) were added. The reaction mixture was shaked at room temperature for 5 minutes and then centrifuged at 5,000×g at 5° C. for 10 minutes. The supernatant separated from phenol layer and denaturated protein layer was again added with half the volume of the above phenol-cresol mixture and shaked for 5 minutes at room temperature.

The supernatant obtained by centrifugation was dialyzed against 5 l of 2 fold the concentration of SSC solution (pH 7.0) containing 0.05% sodium dodecyl sulfate (hereinafter referred to as SDS) at room temperature for one hour, and further dialyzed for one hour after exchanging the outside solution. Thereafter, the outside solution was replaced by 5 l of 0.01 fold the concentration of SSC (pH 7.0) and dyalysis was carried out at 2° to 5° C. overnight. The dialysate (890 ml) was ultrafiltrated using hollow fiber membrane filter to concentrate to 19 ml.

To 19 ml of the ultrafiltrated concentrate, 19 g of CsCl was dissolved. Subsequently, the total volume was adjusted to 26 ml by the addition of 0.01 M Tris-HCl buffer (pH 7.5) containing CsCl in a proportion of 1 g per 1 ml of the buffer solution. The solution (26 ml) was layed onto 7.8 ml of 5.7 M CsCl (pH 6.5) containing 0.1 M EDTA, and then 1.3 ml of 0.1 M Tris-HCl buffer (pH 7.5) was overlayed and centrifuged. The centrifugation was carried out with Spinco SW 27 rotor at 27,000 r.p.m. (130,000×g) at 15° C. for 15 hours.

After centrifugation the supernatant was removed, and the RNA in the clear pellet was dissolved in 3 ml of 0.01 M Tris-HCl buffer (pH 7.5). The resulting solution was cooled in an ice-bath, and two volumes of cooled ethyl alcohol was added and allowed to stand for one hour at −20° C. Thereafter, the precipitate produced was collected by low-speed centrifugation. The supernatant was removed and the precipitate was dissolved again in 0.01 M Tris-HCl buffer (pH 7.5).

The yield of purified RNA was 8.6 mg as calculated from the relationship.

$$A260 = 22$$

wherein A260 is an absorbance at 260 nm of 1 mg/ml RNA solution.

When 50% TCA was added, about 80% of the purified RNA was precipitated as TCA-insoluble fraction. Sedimentation coefficient of purified RNA measured by sucrose density gradient centrifugation using mouse L cell ribosomal RNA as a standard was apploximately 12 s.

(4) Annealing of RNA

Three mg of purified RNA was dissolved in 4.8 ml of 0.01 M Tris-HCl buffer (pH 7.5), and 1.2 ml of 10 fold the concentration of SSC (pH 7.0) was added so that the cencentration of RNA in 2 fold the concentration of SSC became 500 μg/ml. The solution thus obtained was placed in a glass test tube with stopper, heated at 100° C. for 5 minutes, cooled quickly in an ice bath, and thereafter, placed in a water bath at 85° C. The temperature of the water bath was gradually decreased to 65° C. over 2 hours, and the reaction was further carried out at 65° C. for 4 hours. Thereafter, the heater source of the water bath was turned off, and allowed to stand overnight to cool gradually to room temperature.

The sedimentation coefficient of the annealed RNA was determined by sucrose density gradient centrifugation method. As a result, a peak was observed at 12 s with the result that almost no difference was observed as compared with that before annealing. However, a small peak was newly observed in the region above 28 s.

Ribonuclease resistance of the annealed RNA (amount of RNA-RNA hybrid; amount of double-stranded moiety) was determined according to the method of Gumport et al. Thirty μg of the annealed RNA was treated with 30 μg of bovine pancreatic ribonuclease and 3 μg of ribonuclease-$T_1$ in a 2 fold the concentration of SSC (pH 7.0) at 37° C. for 30 minutes with the result that 13.3% of TCA-insoluble fraction was collected on millipore filter (0.45 μm) without being digested. On the other hand, 30 μg of the sample, which was heated in 0.3 fold the concentration of SSC at 100° C. for 5 minutes and quickly cooled in an ice bath, was subjected to ribonuclease treatment in 2 folds the concentration of SSC as mentioned above, with the result that 2.3% of TCA-insoluble fraction was collected on the filter without being digested.

The annealed RNA was recovered by ethanol precipitation according to conventional procedure [Parish & Kirby, Biochim. Biophys. Acta, 129, 554, (1966)]. The precipitate was dialyzed against distilled water, and the dialyzate was sterilized by filtration, divided into vials, and finally subjected to lyophilization. The preparations thus obtained are IF inducer having physical, chemical, and biological properties as mentioned above as well as in Experimental Examples 1 to 5.

EXAMPLE 2

(1) Isolation and Purification of Human Placenta DNA

It was effected by the same purification method as in Example 1.

(2) Purification of E. coli RNA polymerase

E. Coli K-12 strain was grown in Nutrient Broth using a Jar Fermenter, harvested at a late logarithmic phase of growth, and stored frozen at −20° C. Two hundred fifty grams of the cells was suspended in 750 ml of Grinding buffer (0.05 M Tris-HCl (pH 7.9) buffer containing 5% (V/V) glycerol, 2 mM EDTA, 0.1 mM dithiothreitol, 1 mM 2-mercaptoethanol, 0.233 M NaCl, 130 μg/ml hen egg white lyzozyme, and 23 μg/ml phenylmethanesulphonyl fluoride), and allowed to stand 8° C. for 20 minutes. Thereafter, 0.0125 volume of 4% DOC (sodium deoxychloate) was added and the mixture was stirred for 30 seconds. After being allowed to stand for 20 minutes, it was stirred again for 30 seconds. Thereafter, 1,000 ml of TGED+0.2 M NaCl ("TGED" means 0.01 M Tris-HCl buffer (pH 7.9) containing 5% (V/V) glycerol, 0.1 mM EDTA and 0.1 mM dithiothreitol; "TGED+0.2 M NaCl" means "TGED" containing 0.2 M NaCl.) were added and stirred vigorously for 5 minutes. The suspension was centrifuged at 10,000×g at 4° C. for 45 minutes. To the supernatant thus obtained, 0.075 volume of 5% Polymin P (Fluka A.G., Switzerland) (pH 7.9) was added. Five minutes later, the precipitate formed was collected by centrifugation at 6,000×g at 4° C. for 15 minutes. The precipitate was homogenized in TGED+0.5 M NaCl (TGED containing 0.5 M NaCl), and the homogenate was stirred at 4° C. for 10 minutes. The homogenate was centrifuged at 6,000×g at 4° C. for 30 minutes. The precipitate obtained was homogenized in TGED+1.0 M NaCl (TGED containing 1.0 M NaCl), and stirred at 4° C. for 10 minutes. The homogenate was centrifuged at 6,000×g at 4° C. for 30 minutes. To the supernatant thus obtained, ammonium sulfate was added in a proportion of 35 g/100 ml, and stirred at 4° C. for 30 minutes. Thereafter, the suspension was centrifuged at 10,000×g at 4° C. for 45 minutes. The precipitate thus obtained was dissolved in 700 ml of TGED.

The solution was passed through calf thymus DNA-agarose column (2.6×15 cm) prepared according to the method of Schallar et al. (Eur. J. Biochem., 26, 474 (1972)), to adsorb RNA polymerase. The column was washed with 500 ml of TGED+0.15 M NaCl (TGED containing 0.15 M NaCl), and then with 500 ml of TGED+0.3 M NaCl (TGED containing 0.3 M NaCl). Thereafter, 500 ml of TGED+1.2 M NaCl (TGED containing 1.2 M NaCl) was passed through the column to elute RNA polymerase. To the eluate ammonium sulfate was added in a proportion of 35 g/100 ml, and stirred at 4° C. for 30 minutes. The suspension formed was centrifuged at 10,000×g at 4° C. for 30 minutes. The precipitate thus obtained was dissolved in 7 ml of TGED+0.5 M NaCl+30% glycerol (TGED+0.5 M NaCl with the exception that including 30% glycerol instead of 5%). The solution was divided into 2 to 3 equal parts, and each part was subjected to gel filtration with Bio Gel A 5 m [Polyacrylamidegel: Biogel Co. (U.S.A.)] column (2×110 cm) equilibrated with TGED+0.5 M NaCl. Elution was carried out with TGED+0.5 M NaCl. The fractions having RNA polymerase activity in the eluate were collected and used for RNA synthesis.

The specific activity of the RNA polymerase thus obtained was 320 units/mg protein as determined according to the method of Burgess (J. Biol. Chem., 244, 6160) using calf thymus DNA as template.

One unit of enzyme activity was defined as the amount catalyzing the incorporation of 1 n mole of $^{14}$C-ATP into TCA-insoluble material during 10 minutes of incubation.

The absorbance ratio (A280/A260) between 280 nm and 260 nm was 1.86. Total activity of RNA polymerase obtained from 250 g of frozen cells was 30,000 units, and the total amounts of proteins wee 96 mg.

(3) Synthesis, Isolation and Purification of RNA

The reagents for RNA synthesis system are shown in Table 7. Each reagent was dissolved in 0.04 M Tris-HCl buffer (pH 7.9).

TABLE 7

| Reagents in RNA synthesis system, Total 150 ml. | | |
|---|---|---|
| Reagents | Concentration | Total amounts |
| RNA Polymerase | 20 units/ml | 3,000 units |
| Human placenta DNA | 200 μg/ml | 30 mg |
| ATP | 0.6 mM | 90 μmoles |
| CTP | 0.6 mM | 90 μmoles |
| GTP | 0.6 mM | 90 μmoles |
| UTP | 0.6 mM | 90 μmoles |
| KCl | 50 mM | 7.5 m moles |
| $MnCl_2$ | 1 mM | 150 μmoles |
| $MgCl_2$ | 4 mM | 600 μmoles |
| 2-mercaptoethanol | 0.5 mM | 75 μmoles |
| Tris-HCl pH 7.9 | 0.04 M | 6 m moles |

The reagents listed above were mixed well and incubated for 3 hours at 37° C. Thereafter the reaction mixture was cooled in an ice bath to terminate the reaction, and heated for 5 minutes at 65° C. to inactivate RNA polymerase.

The reaction mixture was cooled to about 37° C. with tapped water, and then 16.7 ml of 0.1 M MgCl₂ was added to bring the solution to 10 mM. Further 1.7 mg of deoxyribonuclease (free of ribonuclease) was added and incubated at 37° C. for 30 minutes to digest DNA.

The reaction mixture was heated at 100° C. for 3 minutes to inactivate deoxyribonuclease, and then cooled to room temperature with tapped water. Thereafter, 170 ml of two-fold the concentration of SSC (pH 7.0) and 340 ml of phenol-cresol mixture (composition: phenol 500 g, m-cresol 70 ml, water 55 ml, 8-hydroxyquinoline 0.5 g) were added. The reaction mixture was shaked at room temperature for 5 minutes, and then centrifuged at 5,000×g at 5° C. for 10 minutes. The supernatant separated from phenol layer and denaturated protein layer was added with half the volume of the above phenol-cresol mixture and shaked for 5 minutes at room temperature.

The emulsion was centrifuged, and the supernatant was dialyzed against 5 l of two-fold the concentration of SSC (pH 7.5) containing 0.05% SDS at room temperature for one hour, and further dialyzed for one hour after exchanging the outside solution. Thereafter, the outside solution was replaced by 5 l of 0.01 fold the concentration of SSC (pH 7.0) and dialysis was carried out at 2° to 5° C. overnight. The dialysate (310 ml) was ultrafiltrated using hollow fiber membrane filter to concentrate to 19 ml.

To 19 ml of the ultrafiltrated concentrate, 19 g of CsCl was dissolved. Subsequently, the total volume was adjusted to 26 ml by the addition of 0.01 M Tris-HCl buffer (pH 7.5) containing CsCl in a proportion of 1 g per 1 ml of the buffer solution. The solution (26 ml) was layed onto 7.8 ml of 5.7 M CsCl (pH 6.5) containing 0.1 M EDTA, and then 1.3 ml of 0.1 M Tris-HCl buffer (pH 7.5) was overlayed and centrifuged. The centrifugation was carried out with Spinco SW 27 rotor at 27,000 r.p.m. (130,000×g) at 15° C. for 15 hours.

After centrifugation the supernatant was removed, and the RNA in the clear pellet was dissolved in 3 ml of 0.01 M Tris-HCl buffer (pH 7.5). The resulting solution was cooled in an ice-bath, and two volumes of cooled ethyl alcohol was added and allowed to stand for one hour at −20° C. Thereafter, the precipitate produced was collected by low-speed centrifugation. The supernatant was removed and the precipitate was dissolved again in 0.01 M Tris-HCl buffer solution (pH 7.5).

The yield of purified RNA was 9.0 mg as calculated from the relationship, $$A_{260} = 22$$

wherein $A_{260}$ is an absorbance at 260 nm of 1 mg/ml RNA solution.

When 50% TCA was added, about 90% of the purified RNA was precipitated as TCA-insoluble fraction. Sedimentation coefficient of purified RNA measured by sucrose density gradient centrifugation using mouse L cell ribosomal RNA as a standard was approximately 11 s.

(4) Annealing of RNA

Three mg of purified RNA was dissolved in 12.0 ml of 0.01 M Tris-HCl buffer (pH 7.5), and 3.0 ml of 10 fold the concentration of SSC (pH 7.0) was added so that the concentration of RNA in 2 fold the concentration of SSC became 220 μg/ml. The solution thus obtained was placed in a glass test tube with stopper, heated at 100° C. for 5 minutes, cooled quickly in an ice bath, and thereafter, placed in a water bath at 85° C. The temperature of the water bath was gradually decreased to 65° C. over 2 hours, and the reaction was further carried out at 65° C. for 4 hours. Thereafter, the heater source of the water bath was turned off, and allowed to stand overnight to cool gradually to room temperature.

The sedimentation coefficient of the annealed RNA was determined by sucrose density gradient centrifugation method. As a result, a peak was observed at 11 s with the result that almost no difference was observed as compared with that before annealing. However, a small peak was newly observed in the region above 28 s.

Ribonuclease resistance of the annealed RNA amount of RNA-RNA hybrid; amount of double-standed moiety) was determined according to the method of Gumport et al. Thirty μg of the annealed RNA was treated with 30 μg of bovine pancreatic ribonuclease and 3 μg of ribonuclease-T₁ in a 2 fold the concentration of SSC (pH 7.0) at 37° C. for 30 minutes with the result that 12.0% of TCA-insoluble fraction was collected on millipore filter (0.45 μm) without being digested. On the other hand, 30 μg of the sample, which was heated in 0.3 fold the concentration of SSC at 100° C. for 5 minutes and quickly cooled in an ice bath, was subjected to ribonuclease treatment as mentioned above, with the result that 3.3% of TCA-insoluble fraction was collected on the filter without being digested.

The annealed RNA was recovered by ethanol precipitation according to conventional procedure. [Parish & Kirby, Biochim. Biophys. Acta, 129, 554, (1966)] The precipitate was dialyzed against distilled water, the dialyzate was sterilized by filtration, divided into vials, and finally subjected to lyophilization. The base composition of the purified RNA thus obtained was 27.3% of adenylic acid, 21.5% of guanylic acid, 18.5% of cytidylic acid, and 32.7% of uridylic acid.

What is claimed is:

1. A double-stranded RNA enzymatically synthesized using native human DNA of human placenta as template, of which the double-stranded moiety is in an amount of at least about 4% between their molecules, the molecular weight is mainly 11–13s in terms of sedimentation coefficient as measured by means of sucrose density gradient centrifugation, the base composition is 27.0 to 37.5% of adenylic acid, 20.6 to 24.7% of guanylic acid, 16.8 to 24.3% of cytidylic acid and 27.8 to 32.7% of uridylic acid, the buoyant density in Cs₂SO₄ is 1.653–1.640, the thermal denaturation (Tm) in 0.1 fold the concentration of SSC is 71° C., having the ultraviolet absorption spectrum substantially as shown in FIG. 2, thermal denaturation substantially as shown in FIG. 3 and the absorbance ratio at 25°–90° C. substantially as shown in FIG. 4.

2. A process for enzymatically synthesizing a double-stranded RNA of claim 1 using native human DNA as template, which comprises:

(1) reacting ATP, GTP, CTP and UTP with with one another in the presence of native human DNA of human placenta as template by catalytic action of an active RNA polymerase of *Microoccucus lysodeiticus* or of *Escherichia coli* for 2 to 4 hours at 20° to 40° C. in a tris-HCl buffer solution at pH of 7.0 to 8.0 to form RNA and then terminating the reaction, (2) subjecting the formed RNA to treatment to free it from protein,
(3) concentrating the RNA from step (2),
(4) centrifuging the resulting RNA on a CsCl cushion followed by ethanol-precipitation,
(5) dissolving the centrifuged RNA from step (4) in a compatible saline solution at a pH of from 6.5 to 7.5; and
(6) heating the resulting RNA at a temperature of 70° to 100° C. then rapidly cooling to room temperature or below to anneal the resulting RNA.

3. A double stranded RNA prepared by the process of claim 2.

4. An interferon inducer containing an effective amount of double-stranded RNA enzymatically synthesized using native human DNA of human placenta as template, of which the double-stranded moiety is in an amount of at least about 4% between their molecules, the molecular weight is mainly 11–13s in terms of sedimentation coefficient as measured by means of sucrose density gradient centrifugation, the base composition is 27.0 to 30.5% of adenylic acid, 20.6 to 24.7% of guanylic acid, 16.8 to 24.3% of cytidylic acid and 27.8 to 32.7% of uridylic acid, the buoyant density in $Cs_2SO_4$ is 1.653–1.640 the thermal denaturation in 0.1 fold the concentration of SSC is 71° C., having the ultraviolet absorption spectrum substantially as shown in FIG. 2, thermal denaturation substantially as shown in FIG. 3 and the absorbance ratio at 25°–90° C. substantially as shown in FIG. 4.

* * * * *